United States Patent
Orszulak

(10) Patent No.: US 8,187,262 B2
(45) Date of Patent: *May 29, 2012

(54) DUAL SYNCHRO-RESONANT ELECTROSURGICAL APPARATUS WITH BI-DIRECTIONAL MAGNETIC COUPLING

(75) Inventor: James H. Orszulak, Nederland, CO (US)

(73) Assignee: Covidien AG (CH)

( * ) Notice: Subject to any disclaimer, the term of this patent is extended or adjusted under 35 U.S.C. 154(b) by 398 days.

This patent is subject to a terminal disclaimer.

(21) Appl. No.: 12/477,320

(22) Filed: Jun. 3, 2009

(65) Prior Publication Data

US 2009/0237169 A1    Sep. 24, 2009

Related U.S. Application Data

(63) Continuation of application No. 12/392,176, filed on Feb. 25, 2009, which is a continuation of application No. 11/338,309, filed on Jan. 24, 2006, now Pat. No. 7,513,896.

(51) Int. Cl.
    *A61B 18/10* (2006.01)
(52) U.S. Cl. .......................... 606/34; 606/32
(58) Field of Classification Search .............. 606/32, 606/34–40
    See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |

(Continued)

FOREIGN PATENT DOCUMENTS

DE          179607          3/1905

(Continued)

OTHER PUBLICATIONS

International Search Report EP 07 00 1484.0 dated Jun. 14, 2010.

(Continued)

*Primary Examiner* — Michael Peffley
*Assistant Examiner* — Samantha Good

(57) ABSTRACT

An electrosurgical generator is disclosed. The electrosurgical generator includes a power supply for generating a DC voltage. The electrosurgical generator also includes a first parallel inductor-capacitor circuit being driven by a first signal at a first predetermined frequency and a second parallel inductor-capacitor circuit driven by a second signal at the first predetermined frequency phase shifted 180 degrees. The electrosurgical generator further includes a series inductor-capacitor resonant circuit operably connected in series with a primary winding of a transformer. The first and second parallel inductor-capacitor circuits are operably connected to the transformer, such that the first inductor-capacitor circuit generates a positive half sine wave and the second inductor-capacitor circuit generates a 180 degrees phase-shifted positive half sine wave to generate a full sine wave in a secondary winding of the transformer.

19 Claims, 3 Drawing Sheets

U.S. PATENT DOCUMENTS

| | | |
|---|---|---|
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko et al. |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gonser |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Patterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,767,999 A | 8/1988 | VerPlanck |
| 4,768,969 A | 9/1988 | Bauer et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |
| 4,966,597 A | 10/1990 | Cosman |
| 4,969,885 A | 11/1990 | Farin |
| 4,992,719 A | 2/1991 | Harvey |
| 4,993,430 A | 2/1991 | Shimoyama et al. |
| 4,995,877 A | 2/1991 | Ams et al. |

| | | | | | |
|---|---|---|---|---|---|
| 5,015,227 A | 5/1991 | Broadwin et al. | 5,432,459 A | 7/1995 | Thompson |
| 5,024,668 A | 6/1991 | Peters et al. | 5,433,739 A | 7/1995 | Sluijter et al. |
| 5,044,977 A | 9/1991 | Vindigni | 5,436,566 A | 7/1995 | Thompson |
| 5,067,953 A | 11/1991 | Feucht | 5,438,302 A | 8/1995 | Goble |
| 5,075,839 A | 12/1991 | Fisher et al. | 5,443,463 A | 8/1995 | Stern et al. |
| 5,087,257 A | 2/1992 | Farin | 5,445,635 A | 8/1995 | Denen |
| 5,099,840 A | 3/1992 | Goble et al. | 5,451,224 A | 9/1995 | Goble et al. |
| 5,103,804 A | 4/1992 | Abele et al. | 5,452,725 A | 9/1995 | Martenson |
| 5,108,389 A | 4/1992 | Cosmescu | 5,454,809 A | 10/1995 | Janssen |
| 5,108,391 A | 4/1992 | Flachenecker | 5,458,597 A | 10/1995 | Edwards et al. |
| 5,119,284 A | 6/1992 | Fisher et al. | 5,462,521 A | 10/1995 | Brucker et al. |
| 5,122,137 A | 6/1992 | Lennox | 5,472,441 A | 12/1995 | Edwards et al. |
| 5,133,711 A | 7/1992 | Hagen | 5,472,443 A | 12/1995 | Cordis et al. |
| 5,151,102 A | 9/1992 | Kamiyama et al. | 5,474,464 A | 12/1995 | Drewnicki |
| 5,152,762 A | 10/1992 | McElhenney | 5,480,399 A | 1/1996 | Hebborn |
| 5,157,603 A | 10/1992 | Scheller et al. | 5,483,952 A | 1/1996 | Aranyi |
| 5,160,334 A | 11/1992 | Billings et al. | 5,496,312 A | 3/1996 | Klicek |
| 5,161,893 A | 11/1992 | Shigezawa et al. | 5,496,313 A | 3/1996 | Gentelia et al. |
| 5,167,658 A | 12/1992 | Ensslin | 5,496,314 A | 3/1996 | Eggers |
| 5,167,659 A | 12/1992 | Ohtomo et al. | 5,500,012 A | 3/1996 | Brucker et al. |
| 5,190,517 A | 3/1993 | Zieve et al. | 5,500,616 A | 3/1996 | Ochi |
| 5,196,008 A | 3/1993 | Kuenecke | 5,511,993 A | 4/1996 | Yamada et al. |
| 5,196,009 A | 3/1993 | Kirwan, Jr. | 5,514,129 A | 5/1996 | Smith |
| 5,201,900 A | 4/1993 | Nardella | 5,520,684 A | 5/1996 | Imran |
| 5,207,691 A | 5/1993 | Nardella | 5,531,774 A | 7/1996 | Schulman et al. |
| 5,230,623 A | 7/1993 | Guthrie et al. | 5,534,018 A | 7/1996 | Wahlstrand et al. |
| 5,233,515 A | 8/1993 | Cosman | 5,536,267 A | 7/1996 | Edwards et al. |
| 5,234,427 A | 8/1993 | Ohtomo et al. | 5,540,677 A | 7/1996 | Sinofsky |
| 5,249,121 A | 9/1993 | Baum et al. | 5,540,681 A | 7/1996 | Strul et al. |
| 5,249,585 A | 10/1993 | Turner et al. | 5,540,682 A | 7/1996 | Gardner et al. |
| 5,254,117 A | 10/1993 | Rigby et al. | 5,540,683 A | 7/1996 | Ichikawa |
| RE34,432 E | 11/1993 | Bertrand | 5,540,684 A | 7/1996 | Hassler, Jr. |
| 5,267,994 A | 12/1993 | Gentelia et al. | 5,541,376 A | 7/1996 | Ladtkow et al. |
| 5,267,997 A | 12/1993 | Farin | 5,545,161 A | 8/1996 | Imran |
| 5,281,213 A | 1/1994 | Milder et al. | 5,556,396 A | 9/1996 | Cohen et al. |
| 5,282,840 A | 2/1994 | Hudrlik | 5,558,671 A | 9/1996 | Yates |
| 5,290,283 A | 3/1994 | Suda | 5,562,720 A | 10/1996 | Stern et al. |
| 5,295,857 A | 3/1994 | Toly | 5,569,242 A | 10/1996 | Lax et al. |
| 5,300,068 A | 4/1994 | Rosar et al. | 5,571,147 A | 11/1996 | Sluijter et al. |
| 5,300,070 A | 4/1994 | Gentelia | 5,573,533 A | 11/1996 | Strul |
| 5,304,917 A | 4/1994 | Somerville | 5,584,830 A | 12/1996 | Ladd et al. |
| 5,318,563 A | 6/1994 | Malis et al. | 5,588,432 A | 12/1996 | Crowley |
| 5,323,778 A | 6/1994 | Kandarpa et al. | 5,596,466 A | 1/1997 | Ochi |
| 5,324,283 A | 6/1994 | Heckele | 5,599,344 A | 2/1997 | Paterson |
| 5,330,518 A | 7/1994 | Neilson et al. | 5,599,345 A | 2/1997 | Edwards et al. |
| 5,334,183 A | 8/1994 | Wuchinich | 5,599,348 A | 2/1997 | Gentelia et al. |
| 5,334,193 A | 8/1994 | Nardella | 5,605,150 A | 2/1997 | Radons et al. |
| 5,341,807 A | 8/1994 | Nardella | 5,609,560 A | 3/1997 | Ichikawa et al. |
| 5,342,356 A | 8/1994 | Ellman et al. | 5,613,966 A | 3/1997 | Makower et al. |
| 5,342,357 A | 8/1994 | Nardella | 5,620,481 A | 4/1997 | Desai et al. |
| 5,342,409 A | 8/1994 | Mullett | 5,626,575 A | 5/1997 | Crenner |
| 5,346,406 A | 9/1994 | Hoffman et al. | 5,628,745 A | 5/1997 | Bek |
| 5,346,491 A | 9/1994 | Oertli | 5,628,771 A | 5/1997 | Mizukawa et al. |
| 5,348,554 A | 9/1994 | Imran et al. | 5,643,330 A | 7/1997 | Holsheimer et al. |
| 5,370,645 A | 12/1994 | Klicek et al. | 5,647,869 A | 7/1997 | Goble et al. |
| 5,370,672 A | 12/1994 | Fowler et al. | 5,647,871 A | 7/1997 | Levine et al. |
| 5,370,675 A | 12/1994 | Edwards et al. | 5,651,780 A | 7/1997 | Jackson et al. |
| 5,372,596 A | 12/1994 | Klicek et al. | 5,658,322 A | 8/1997 | Fleming |
| 5,383,874 A | 1/1995 | Jackson | 5,660,567 A | 8/1997 | Nierlich et al. |
| 5,383,876 A | 1/1995 | Nardella | 5,664,953 A | 9/1997 | Reylek |
| 5,383,917 A | 1/1995 | Desai et al. | 5,674,217 A | 10/1997 | Wahlstrom et al. |
| 5,385,148 A | 1/1995 | Lesh et al. | 5,678,568 A | 10/1997 | Uchikubo et al. |
| 5,400,267 A | 3/1995 | Denen et al. | 5,681,307 A | 10/1997 | McMahan |
| 5,403,311 A | 4/1995 | Abele et al. | 5,685,840 A | 11/1997 | Schechter et al. |
| 5,403,312 A | 4/1995 | Yates et al. | 5,688,267 A | 11/1997 | Panescu et al. |
| 5,409,000 A | 4/1995 | Imran | 5,693,042 A | 12/1997 | Boiarski et al. |
| 5,409,485 A | 4/1995 | Suda | 5,693,078 A | 12/1997 | Desai et al. |
| 5,413,573 A | 5/1995 | Koivukangas | 5,694,304 A | 12/1997 | Telefus et al. |
| 5,414,238 A | 5/1995 | Steigerwald et al. | 5,695,494 A | 12/1997 | Becker |
| 5,417,719 A | 5/1995 | Hull et al. | 5,696,441 A | 12/1997 | Mak et al. |
| 5,422,567 A | 6/1995 | Matsunaga | 5,697,925 A | 12/1997 | Taylor |
| 5,422,926 A | 6/1995 | Smith et al. | 5,697,927 A | 12/1997 | Imran et al. |
| 5,423,808 A | 6/1995 | Edwards et al. | 5,702,386 A | 12/1997 | Stern et al. |
| 5,423,809 A | 6/1995 | Klicek | 5,702,429 A | 12/1997 | King |
| 5,423,810 A | 6/1995 | Goble et al. | 5,707,369 A | 1/1998 | Vaitekunas et al. |
| 5,423,811 A | 6/1995 | Imran et al. | 5,712,772 A | 1/1998 | Telefus et al. |
| 5,425,704 A | 6/1995 | Sakurai et al. | 5,713,896 A | 2/1998 | Nardella |
| 5,429,596 A | 7/1995 | Arias et al. | 5,718,246 A | 2/1998 | Vona |
| 5,430,434 A | 7/1995 | Lederer et al. | 5,720,742 A | 2/1998 | Zacharias |

| Patent No. | Date | Inventor |
|---|---|---|
| 5,720,744 A | 2/1998 | Eggleston |
| 5,722,975 A | 3/1998 | Edwards et al. |
| 5,729,448 A | 3/1998 | Haynie et al. |
| 5,733,281 A | 3/1998 | Nardella |
| 5,735,846 A | 4/1998 | Panescu et al. |
| 5,738,683 A | 4/1998 | Osypka |
| 5,743,900 A | 4/1998 | Hara |
| 5,743,903 A | 4/1998 | Stern et al. |
| 5,749,869 A | 5/1998 | Lindenmeier et al. |
| 5,749,871 A | 5/1998 | Hood et al. |
| 5,755,715 A | 5/1998 | Stern |
| 5,766,153 A | 6/1998 | Eggers et al. |
| 5,766,165 A | 6/1998 | Gentelia et al. |
| 5,769,847 A | 6/1998 | Panescu |
| 5,772,659 A | 6/1998 | Becker et al. |
| 5,788,688 A | 8/1998 | Bauer et al. |
| 5,792,138 A | 8/1998 | Shipp |
| 5,797,902 A | 8/1998 | Netherly |
| 5,807,253 A | 9/1998 | Dumoulin et al. |
| 5,810,804 A | 9/1998 | Gough et al. |
| 5,814,092 A | 9/1998 | King |
| 5,817,091 A | 10/1998 | Nardella et al. |
| 5,817,093 A | 10/1998 | Williamson, IV et al. |
| 5,820,568 A | 10/1998 | Willis |
| 5,827,271 A | 10/1998 | Buysse et al. |
| 5,830,212 A | 11/1998 | Cartmell |
| 5,836,909 A | 11/1998 | Cosmescu |
| 5,836,943 A | 11/1998 | Miller, III |
| 5,836,990 A | 11/1998 | Li |
| 5,843,019 A | 12/1998 | Eggers et al. |
| 5,843,075 A | 12/1998 | Taylor |
| 5,846,236 A | 12/1998 | Lindenmeier et al. |
| 5,849,010 A | 12/1998 | Wurzer et al. |
| 5,853,409 A | 12/1998 | Swanson et al. |
| 5,860,832 A | 1/1999 | Wayt et al. |
| 5,865,788 A | 2/1999 | Edwards et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A | 2/1999 | Kannenberg et al. |
| 5,891,142 A | 4/1999 | Eggers et al. |
| 5,897,552 A | 4/1999 | Edwards et al. |
| 5,906,614 A | 5/1999 | Stern et al. |
| 5,908,444 A | 6/1999 | Azure |
| 5,913,882 A | 6/1999 | King |
| 5,921,982 A | 7/1999 | Lesh et al. |
| 5,925,070 A | 7/1999 | King et al. |
| 5,931,836 A | 8/1999 | Hatta et al. |
| 5,938,690 A | 8/1999 | Law et al. |
| 5,944,553 A | 8/1999 | Yasui et al. |
| 5,948,007 A | 9/1999 | Starkebaum et al. |
| 5,951,545 A | 9/1999 | Schilling |
| 5,951,546 A | 9/1999 | Lorentzen |
| 5,954,686 A | 9/1999 | Garito et al. |
| 5,954,717 A | 9/1999 | Behl et al. |
| 5,954,719 A | 9/1999 | Chen et al. |
| 5,957,961 A | 9/1999 | Maguire et al. |
| 5,959,253 A | 9/1999 | Shinchi |
| 5,961,344 A | 10/1999 | Rosales et al. |
| 5,964,746 A | 10/1999 | McCary |
| 5,971,980 A | 10/1999 | Sherman |
| 5,971,981 A | 10/1999 | Hill et al. |
| 5,976,128 A | 11/1999 | Schilling et al. |
| 5,983,141 A | 11/1999 | Sluijter et al. |
| 6,007,532 A | 12/1999 | Netherly |
| 6,010,499 A | 1/2000 | Cobb |
| 6,013,074 A | 1/2000 | Taylor |
| 6,014,581 A | 1/2000 | Whayne et al. |
| 6,017,338 A | 1/2000 | Brucker et al. |
| 6,022,346 A | 2/2000 | Panescu et al. |
| 6,022,347 A | 2/2000 | Lindenmeier et al. |
| 6,033,399 A | 3/2000 | Gines |
| 6,039,731 A | 3/2000 | Taylor et al. |
| 6,039,732 A | 3/2000 | Ichikawa et al. |
| 6,041,260 A | 3/2000 | Stern et al. |
| 6,044,283 A | 3/2000 | Fein et al. |
| 6,053,910 A | 4/2000 | Fleenor |
| 6,053,912 A | 4/2000 | Panescu et al. |
| 6,055,458 A | 4/2000 | Cochran et al. |
| 6,056,745 A | 5/2000 | Panescu et al. |
| 6,056,746 A | 5/2000 | Goble et al. |
| 6,059,781 A | 5/2000 | Yamanashi et al. |
| 6,063,075 A | 5/2000 | Mihori |
| 6,063,078 A | 5/2000 | Wittkampf |
| 6,066,137 A | 5/2000 | Greep |
| 6,068,627 A | 5/2000 | Orszulak et al. |
| 6,074,089 A | 6/2000 | Hollander et al. |
| 6,074,386 A | 6/2000 | Goble et al. |
| 6,074,388 A | 6/2000 | Tockweiler et al. |
| 6,080,149 A | 6/2000 | Huang et al. |
| 6,088,614 A | 7/2000 | Swanson |
| 6,093,186 A | 7/2000 | Goble |
| 6,102,497 A | 8/2000 | Ehr et al. |
| 6,102,907 A | 8/2000 | Smethers et al. |
| 6,113,591 A | 9/2000 | Whayne et al. |
| 6,113,592 A | 9/2000 | Taylor |
| 6,113,593 A | 9/2000 | Tu et al. |
| 6,113,596 A | 9/2000 | Hooven |
| 6,123,701 A | 9/2000 | Nezhat |
| 6,123,702 A | 9/2000 | Swanson et al. |
| 6,132,429 A | 10/2000 | Baker |
| 6,142,992 A | 11/2000 | Cheng et al. |
| 6,155,975 A | 12/2000 | Urich et al. |
| 6,162,184 A | 12/2000 | Swanson et al. |
| 6,162,217 A | 12/2000 | Kannenberg et al. |
| 6,165,169 A | 12/2000 | Panescu et al. |
| 6,171,304 B1 | 1/2001 | Netherly et al. |
| 6,183,468 B1 | 2/2001 | Swanson et al. |
| 6,186,147 B1 | 2/2001 | Cobb |
| 6,188,211 B1 | 2/2001 | Rincon-Mora et al. |
| 6,193,713 B1 | 2/2001 | Geistert et al. |
| 6,197,023 B1 | 3/2001 | Muntermann |
| 6,203,541 B1 | 3/2001 | Keppel |
| 6,210,403 B1 | 4/2001 | Klicek |
| 6,216,704 B1 | 4/2001 | Ingle et al. |
| 6,222,356 B1 | 4/2001 | Taghizadeh-Kaschani |
| 6,228,078 B1 | 5/2001 | Eggers et al. |
| 6,228,080 B1 | 5/2001 | Gines |
| 6,228,081 B1 | 5/2001 | Goble |
| 6,231,569 B1 | 5/2001 | Bek et al. |
| 6,232,556 B1 | 5/2001 | Daugherty et al. |
| 6,235,020 B1 | 5/2001 | Cheng et al. |
| 6,235,022 B1 | 5/2001 | Hallock et al. |
| 6,237,604 B1 | 5/2001 | Burnside et al. |
| 6,238,387 B1 | 5/2001 | Miller, III |
| 6,238,388 B1 | 5/2001 | Ellman |
| 6,241,723 B1 | 6/2001 | Heim et al. |
| 6,241,725 B1 | 6/2001 | Cosman |
| 6,243,654 B1 | 6/2001 | Johnson et al. |
| 6,245,061 B1 | 6/2001 | Panescu et al. |
| 6,245,063 B1 | 6/2001 | Uphoff |
| 6,245,065 B1 | 6/2001 | Panescu |
| 6,246,912 B1 | 6/2001 | Sluijter et al. |
| 6,251,106 B1 | 6/2001 | Becker et al. |
| 6,254,422 B1 | 7/2001 | Feye-Hohmann |
| 6,258,085 B1 | 7/2001 | Eggleston |
| 6,261,285 B1 | 7/2001 | Novak et al. |
| 6,261,286 B1 | 7/2001 | Goble et al. |
| 6,267,760 B1 | 7/2001 | Swanson |
| 6,273,886 B1 | 8/2001 | Edwards |
| 6,275,786 B1 | 8/2001 | Daners |
| 6,293,941 B1 | 9/2001 | Strul |
| 6,293,942 B1 | 9/2001 | Goble et al. |
| 6,293,943 B1 | 9/2001 | Panescu et al. |
| 6,296,636 B1 | 10/2001 | Cheng et al. |
| 6,306,131 B1 | 10/2001 | Hareyama et al. |
| 6,306,134 B1 | 10/2001 | Goble et al. |
| 6,309,386 B1 | 10/2001 | Bek |
| 6,322,558 B1 | 11/2001 | Taylor et al. |
| 6,325,799 B1 | 12/2001 | Goble |
| 6,337,998 B1 | 1/2002 | Behl et al. |
| 6,338,657 B1 | 1/2002 | Harper et al. |
| 6,350,262 B1 | 2/2002 | Ashley |
| 6,358,245 B1 | 3/2002 | Edwards |
| 6,364,877 B1 | 4/2002 | Goble et al. |
| 6,371,963 B1 | 4/2002 | Nishtala et al. |
| 6,383,183 B1 | 5/2002 | Sekino et al. |
| 6,391,024 B1 | 5/2002 | Sun et al. |

| | | | | | | |
|---|---|---|---|---|---|---|
| 6,398,779 B1 | 6/2002 | Buysse et al. | | 6,692,489 B1 | 2/2004 | Heim |
| 6,398,781 B1 | 6/2002 | Goble et al. | | 6,693,782 B1 | 2/2004 | Lash |
| 6,402,741 B1 | 6/2002 | Keppel et al. | | 6,695,837 B2 | 2/2004 | Howell |
| 6,402,742 B1 | 6/2002 | Blewett et al. | | 6,696,844 B2 | 2/2004 | Wong et al. |
| 6,402,743 B1 | 6/2002 | Orszulak et al. | | 6,712,813 B2 | 3/2004 | Ellman |
| 6,402,748 B1 | 6/2002 | Schoenman et al. | | 6,730,078 B2 | 5/2004 | Simpson et al. |
| 6,409,722 B1 | 6/2002 | Hoey et al. | | 6,730,079 B2 | 5/2004 | Lovewell |
| 6,413,256 B1 | 7/2002 | Truckai et al. | | 6,730,080 B2 | 5/2004 | Harano |
| 6,416,509 B1 | 7/2002 | Goble et al. | | 6,733,495 B1 | 5/2004 | Bek |
| 6,422,896 B2 | 7/2002 | Aoki et al. | | 6,733,498 B2 | 5/2004 | Paton |
| 6,423,057 B1 | 7/2002 | He et al. | | 6,740,079 B1 | 5/2004 | Eggers |
| 6,426,886 B1 | 7/2002 | Goder | | 6,740,085 B2 | 5/2004 | Hareyama |
| 6,428,537 B1 | 8/2002 | Swanson et al. | | 6,743,225 B2 | 6/2004 | Sanchez et al. |
| 6,436,096 B1 | 8/2002 | Hareyama | | 6,746,284 B1 | 6/2004 | Spink, Jr. |
| 6,440,157 B1 | 8/2002 | Shigezawa et al. | | 6,749,624 B2 | 6/2004 | Knowlton |
| 6,451,015 B1 | 9/2002 | Rittman, III et al. | | 6,755,825 B2 | 6/2004 | Shoenman et al. |
| 6,454,594 B2 | 9/2002 | Sawayanagi | | 6,758,846 B2 | 7/2004 | Goble et al. |
| 6,458,121 B1 | 10/2002 | Rosenstock | | 6,761,716 B2 | 7/2004 | Kadhiresan et al. |
| 6,458,122 B1 | 10/2002 | Pozzato | | 6,783,523 B2 | 8/2004 | Qin |
| 6,464,689 B1 | 10/2002 | Qin et al. | | 6,784,405 B2 | 8/2004 | Flugstad et al. |
| 6,464,696 B1 | 10/2002 | Oyama et al. | | 6,786,905 B2 | 9/2004 | Swanson et al. |
| 6,468,270 B1 | 10/2002 | Hovda et al. | | 6,790,206 B2 | 9/2004 | Panescu |
| 6,468,273 B1 | 10/2002 | Leveen et al. | | 6,792,390 B1 | 9/2004 | Burnside et al. |
| 6,482,201 B1 | 11/2002 | Olsen et al. | | 6,796,980 B2 | 9/2004 | Hall |
| 6,488,678 B2 | 12/2002 | Sherman | | 6,796,981 B2 | 9/2004 | Wham |
| 6,494,880 B1 | 12/2002 | Swanson et al. | | 6,809,508 B2 | 10/2004 | Donofrio |
| 6,497,659 B1 | 12/2002 | Rafert | | 6,818,000 B2 | 11/2004 | Muller et al. |
| 6,498,466 B1 | 12/2002 | Edwards | | 6,824,539 B2 | 11/2004 | Novak |
| 6,506,189 B1 | 1/2003 | Rittman, III et al. | | 6,830,569 B2 | 12/2004 | Thompson |
| 6,508,815 B1 | 1/2003 | Strul | | 6,837,888 B2 | 1/2005 | Ciarrocca et al. |
| 6,511,476 B2 | 1/2003 | Hareyama | | 6,843,682 B2 | 1/2005 | Matsuda et al. |
| 6,511,478 B1 | 1/2003 | Burnside | | 6,843,789 B2 | 1/2005 | Goble |
| 6,517,538 B1 | 2/2003 | Jacob et al. | | 6,849,073 B2 | 2/2005 | Hoey |
| 6,522,931 B2 | 2/2003 | Manker et al. | | 6,855,141 B2 | 2/2005 | Lovewell |
| 6,524,308 B1 | 2/2003 | Muller et al. | | 6,855,142 B2 | 2/2005 | Harano |
| 6,537,272 B2 | 3/2003 | Christopherson et al. | | 6,860,881 B2 | 3/2005 | Sturm |
| 6,544,260 B1 | 4/2003 | Markel et al. | | 6,864,686 B2 | 3/2005 | Novak |
| 6,546,270 B1 | 4/2003 | Goldin et al. | | 6,875,210 B2 | 4/2005 | Refior |
| 6,547,786 B1 | 4/2003 | Goble | | 6,890,331 B2 | 5/2005 | Kristensen |
| 6,557,559 B1 | 5/2003 | Eggers et al. | | 6,893,435 B2 | 5/2005 | Goble |
| 6,558,376 B2 | 5/2003 | Bishop | | 6,899,538 B2 | 5/2005 | Matoba |
| 6,558,377 B2 | 5/2003 | Lee et al. | | 6,923,804 B2 | 8/2005 | Eggers et al. |
| 6,560,470 B1 | 5/2003 | Pologe | | 6,929,641 B2 | 8/2005 | Goble et al. |
| 6,562,037 B2 | 5/2003 | Paton | | 6,936,047 B2 | 8/2005 | Nasab et al. |
| 6,565,559 B2 | 5/2003 | Eggleston | | 6,939,344 B2 | 9/2005 | Kreindel |
| 6,565,562 B1 | 5/2003 | Shah et al. | | 6,939,346 B2 | 9/2005 | Kannenberg et al. |
| 6,575,969 B1 | 6/2003 | Rittman, III et al. | | 6,939,347 B2 | 9/2005 | Thompson |
| 6,578,579 B2 | 6/2003 | Burnside et al. | | 6,942,660 B2 | 9/2005 | Pantera et al. |
| 6,579,288 B1 | 6/2003 | Swanson et al. | | 6,948,503 B2 | 9/2005 | Refior et al. |
| 6,582,427 B1 | 6/2003 | Goble et al. | | 6,958,064 B2 | 10/2005 | Rioux et al. |
| 6,602,243 B2 | 8/2003 | Noda | | 6,962,587 B2 | 11/2005 | Johnson et al. |
| 6,602,252 B2 | 8/2003 | Mollenauer | | 6,966,907 B2 | 11/2005 | Goble |
| 6,611,793 B1 | 8/2003 | Burnside et al. | | 6,974,453 B2 | 12/2005 | Woloszko et al. |
| 6,620,157 B1 | 9/2003 | Dabney et al. | | 6,974,463 B2 | 12/2005 | Magers et al. |
| 6,620,189 B1 | 9/2003 | Machold et al. | | 6,977,495 B2 | 12/2005 | Donofrio |
| 6,623,423 B2 | 9/2003 | Sakurai | | 6,984,231 B2 | 1/2006 | Goble et al. |
| 6,626,901 B1 | 9/2003 | Treat et al. | | 6,989,010 B2 | 1/2006 | Francischelli et al. |
| 6,629,973 B1 | 10/2003 | Wardell et al. | | 6,994,704 B2 | 2/2006 | Qin et al. |
| 6,632,193 B1 | 10/2003 | Davison et al. | | 6,994,707 B2 | 2/2006 | Ellman et al. |
| 6,635,056 B2 | 10/2003 | Kadhiresan et al. | | 7,001,379 B2 | 2/2006 | Behl et al. |
| 6,635,057 B2 | 10/2003 | Harano | | 7,001,381 B2 | 2/2006 | Harano et al. |
| 6,645,198 B1 | 11/2003 | Bommannan et al. | | 7,004,174 B2 | 2/2006 | Eggers et al. |
| 6,648,883 B2 | 11/2003 | Francischelli | | 7,008,369 B2 | 3/2006 | Cuppen |
| 6,651,669 B1 | 11/2003 | Burnside | | 7,008,417 B2 | 3/2006 | Eick |
| 6,652,513 B2 | 11/2003 | Panescu et al. | | 7,008,421 B2 | 3/2006 | Daniel et al. |
| 6,652,514 B2 | 11/2003 | Ellman | | 7,025,764 B2 | 4/2006 | Paton et al. |
| 6,653,569 B1 | 11/2003 | Sung | | 7,033,351 B2 | 4/2006 | Howell |
| 6,656,177 B2 | 12/2003 | Truckai et al. | | 7,041,096 B2 | 5/2006 | Malis et al. |
| 6,663,623 B1 | 12/2003 | Oyama et al. | | 7,044,948 B2 | 5/2006 | Keppel |
| 6,663,624 B2 | 12/2003 | Edwards et al. | | 7,044,949 B2 | 5/2006 | Orszulak et al. |
| 6,663,627 B2 | 12/2003 | Francischelli et al. | | 7,060,063 B2 | 6/2006 | Marion et al. |
| 6,666,860 B1 | 12/2003 | Takahashi | | 7,062,331 B2 | 6/2006 | Zarinetchi et al. |
| 6,672,151 B1 | 1/2004 | Schultz et al. | | 7,063,692 B2 | 6/2006 | Sakurai et al. |
| 6,679,875 B2 | 1/2004 | Honda | | 7,066,933 B2 | 6/2006 | Hagg |
| 6,682,527 B2 | 1/2004 | Strul | | 7,074,217 B2 | 7/2006 | Strul et al. |
| 6,685,700 B2 | 2/2004 | Behl | | 7,083,618 B2 | 8/2006 | Couture et al. |
| 6,685,701 B2 | 2/2004 | Orszulak et al. | | 7,094,231 B1 | 8/2006 | Ellman et al. |
| 6,685,703 B2 | 2/2004 | Pearson et al. | | 7,104,834 B2 | 9/2006 | Robinson et al. |
| 6,689,131 B2 | 2/2004 | McClurken | | RE39,358 E | 10/2006 | Goble |

| Patent No. | Date | Name |
|---|---|---|
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,192,427 B2 | 3/2007 | Chapelon et al. |
| 7,195,627 B2 | 3/2007 | Amoah et al. |
| 7,203,556 B2 | 4/2007 | Daners |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,238,181 B2 | 7/2007 | Daners et al. |
| 7,238,183 B2 | 7/2007 | Kreindel |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | Van Zyl |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,470,272 B2 | 12/2008 | Mulier et al. |
| 7,479,140 B2 | 1/2009 | Ellman et al. |
| 7,491,199 B2 | 2/2009 | Goble |
| 7,491,201 B2 | 2/2009 | Shields et al. |
| 7,513,896 B2 | 4/2009 | Orszulak |
| 7,525,398 B2 | 4/2009 | Nishimura et al. |
| 7,648,499 B2 * | 1/2010 | Orszulak et al. ............... 606/34 |
| 2003/0181898 A1 | 9/2003 | Bowers |
| 2003/0199863 A1 | 10/2003 | Swanson |
| 2004/0015159 A1 | 1/2004 | Slater et al. |
| 2004/0030330 A1 | 2/2004 | Brassell et al. |
| 2004/0068304 A1 | 4/2004 | Paton |
| 2004/0097912 A1 | 5/2004 | Gonnering |
| 2004/0143263 A1 | 7/2004 | Schechter et al. |
| 2004/0172016 A1 | 9/2004 | Bek et al. |
| 2005/0004564 A1 | 1/2005 | Wham |
| 2005/0004634 A1 | 1/2005 | Ricart et al. |
| 2005/0021020 A1 | 1/2005 | Blaha et al. |
| 2005/0109111 A1 | 5/2005 | Manlove et al. |
| 2005/0149151 A1 * | 7/2005 | Orszulak et al. ............... 607/96 |
| 2005/0182398 A1 | 8/2005 | Paterson |
| 2005/0197659 A1 | 9/2005 | Bahney |
| 2005/0203504 A1 | 9/2005 | Wham et al. |
| 2006/0025760 A1 | 2/2006 | Podhajsky |
| 2006/0079871 A1 | 4/2006 | Plaven et al. |
| 2006/0111711 A1 | 5/2006 | Goble |
| 2006/0161148 A1 | 7/2006 | Behnke |
| 2006/0178664 A1 | 8/2006 | Keppel |
| 2006/0224152 A1 | 10/2006 | Behnke et al. |
| 2006/0281360 A1 | 12/2006 | Sartor et al. |
| 2006/0291178 A1 | 12/2006 | Shih |
| 2007/0038209 A1 | 2/2007 | Buysse et al. |
| 2007/0093800 A1 | 4/2007 | Wham et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173813 A1 | 7/2007 | Odom |
| 2007/0208339 A1 | 9/2007 | Arts et al. |
| 2007/0225698 A1 | 9/2007 | Orszulak et al. |
| 2007/0250052 A1 | 10/2007 | Wham |
| 2007/0265612 A1 | 11/2007 | Behnke et al. |
| 2007/0282320 A1 | 12/2007 | Buysse et al. |
| 2008/0015563 A1 | 1/2008 | Hoey et al. |
| 2008/0015564 A1 | 1/2008 | Wham et al. |
| 2008/0039831 A1 | 2/2008 | Odom et al. |
| 2008/0039836 A1 | 2/2008 | Odom et al. |
| 2008/0082094 A1 | 4/2008 | McPherson et al. |
| 2008/0125767 A1 | 5/2008 | Blaha |
| 2008/0177199 A1 | 7/2008 | Podhajsky |
| 2008/0248685 A1 | 10/2008 | Sartor et al. |
| 2008/0281315 A1 | 11/2008 | Gines |
| 2008/0281316 A1 | 11/2008 | Carlton et al. |
| 2008/0287791 A1 | 11/2008 | Orszulak |
| 2008/0287838 A1 | 11/2008 | Orszulak |
| 2009/0018536 A1 | 1/2009 | Behnke |
| 2009/0024120 A1 | 1/2009 | Sartor |
| 2009/0036883 A1 | 2/2009 | Behnke |
| 2009/0069801 A1 | 3/2009 | Jensen et al. |
| 2009/0082765 A1 | 3/2009 | Collins et al. |
| 2009/0157071 A1 | 6/2009 | Wham et al. |
| 2009/0157072 A1 | 6/2009 | Wham et al. |
| 2009/0157073 A1 | 6/2009 | Orszulak |
| 2009/0157075 A1 | 6/2009 | Wham et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |

| | | |
|---|---|---|
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 569130 | 11/1993 |
| EP | 608609 | 8/1994 |
| EP | 694291 | 1/1996 |
| EP | 836868 | 4/1998 |
| EP | 878169 | 11/1998 |
| EP | 1051948 | 11/2000 |
| EP | 1053720 | 11/2000 |
| EP | 1151725 | 11/2001 |
| EP | 1293171 | 3/2003 |
| EP | 1472984 | 11/2004 |
| EP | 1495712 | 1/2005 |
| EP | 1500378 | 1/2005 |
| EP | 1535581 | 6/2005 |
| EP | 1609430 | 12/2005 |
| EP | 1707144 | 3/2006 |
| EP | 1645235 | 4/2006 |
| EP | 880220 | 6/2006 |
| EP | 1707143 | 10/2006 |
| EP | 1744354 | 1/2007 |
| EP | 1810628 | 7/2007 |
| EP | 1810630 | 7/2007 |
| EP | 1810633 | 7/2007 |
| EP | 1854423 | 11/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 1290304 * | 9/1972 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO95/25471 | 9/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO 96/39085 | 12/1996 |
| WO | WO96/39086 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/11648 | 4/1997 |
| WO | WO97/17029 | 5/1997 |
| WO | WO98/07378 | 2/1998 |
| WO | WO98/18395 | 5/1998 |
| WO | WO98/27880 | 7/1998 |
| WO | WO99/12607 | 3/1999 |
| WO | WO02/00129 | 1/2002 |
| WO | WO02/011634 | 2/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/090630 | 11/2003 |
| WO | WO03/090635 | 11/2003 |
| WO | WO03/092520 | 11/2003 |
| WO | WO2004/028385 | 4/2004 |
| WO | WO2004/098385 | 4/2004 |
| WO | WO2004/043240 | 5/2004 |
| WO | WO2004/052182 | 6/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005/060365 | 7/2005 |
| WO | WO2005/060849 | 7/2005 |
| WO | WO2006/050888 | 5/2006 |
| WO | WO2006/105121 | 10/2006 |

OTHER PUBLICATIONS

European Search Report for European Application No: 11188798.0 dated Dec. 9, 2011.
US 6,878,148, 4/2005, Goble et al. (withdrawn).
U.S. Appl. No. 12/057,557, filed Mar. 28, 2009, Wham et al.
U.S. Appl. No. 10/406,690, filed Apr. 3, 2003, Klicek.
U.S. Appl. No. 11/242,458, filed Oct. 3, 2005, Becker et al.
U.S. Appl. No. 10/573,713, filed Mar. 28, 2006, Wham.
U.S. Appl. No. 12/136,620, filed Jun. 10, 2008, Podhajsky et al.
U.S. Appl. No. 12/389,168, filed Feb. 19, 2009, Orszulak.
U.S. Appl. No. 12/351,935, filed Jan. 12, 2009, Podhajsky et al.
U.S. Appl. No. 12/401,981, filed Mar. 11, 2009, Behnke et al.
U.S. Appl. No. 12/351,947, filed Jan. 12, 2009, Podhajsky.
U.S. Appl. No. 12/407,896, filed Mar. 20, 2009, Craig.
U.S. Appl. No. 12/205,525, filed Sep. 5, 2008, Orszulak.
U.S. Appl. No. 12/249,263, filed Oct. 10, 2008, Ward.
U.S. Appl. No. 12/249,218, filed Oct. 10, 2008, Kerr.
U.S. Appl. No. 12/351,970, filed Jan. 12, 2009, Podhajsky et al.
U.S. Appl. No. 12/351,960, filed Jan. 12, 2009, Podhajsky et al.
U.S Appl. No. 12/205,298, filed Sep. 5, 2008, Orszulak.
U.S. Appl. No. 12/351,980, filed Jan. 12, 2009, Podhajsky et al.
U.S. Appl. No. 12/203,734, filed Sep. 3, 2008, Behnke et al.
U.S. Appl. No. 12/242,102, filed Sep. 30, 2008, Brannan et al.
U.S. Appl. No. 12/241,861, filed Sep. 30, 2008, Haley et al.
U.S. Appl. No. 12/242,061, filed Sep. 30, 2008, Brannan et al.
U.S. Appl. No. 12/242,026, filed Sep. 30, 2008, Brannan et al.
U.S. Appl. No. 12/241,905, filed Sep. 30, 2008, Brannan et al.
U.S. Appl. No. 12/241,942, filed Sep. 30, 2008, Brannan et al.
U.S. Appl. No. 12/241,983, filed Sep. 30, 2008, Brannan et al.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Geddes et al., "The Measurement of Physiologic Events by Electrical Impedence" Am. J. MI, Jan. Mar. 1964, pp. 16-27.
Cosman et al., "Methods of Making Nervous System Lesions" in William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/USO4/02961 dated Aug. 2, 2005.

* cited by examiner

DUAL SYNCHRO-RESONANT ELECTROSURGICAL APPARATUS WITH BI-DIRECTIONAL MAGNETIC COUPLING

CROSS-REFERENCE TO RELATED APPLICATION

The present application is a continuation of U.S. patent application Ser. No. 12/392,176 entitled "DUAL SYNCHRO-RESONANT ELECTROSURGICAL APPARATUS WITH BI-DIRECTIONAL MAGNETIC COUPLING:" by Orszulak, filed on Feb. 25, 2009, which is a continuation of U.S. patent application Ser. No. 11/338,309 entitled "DUAL SYNCHRO-RESONANT ELECTROSURGICAL APPARATUS WITH BI-DIRECTIONAL MAGNETIC COUPLING" by Orszulak, filed on Jan. 24, 2006, now U.S. Pat. No. 7,513,896, the entire disclosure of which is incorporated by reference herein.

BACKGROUND

1. Technical Field

The present disclosure relates generally to electrosurgical system, and more specifically, to an electrosurgical generator for delivering high power radiofrequency (RF) energy using multiple resonant inductor-capacitor (LC) networks and a switching module for adjusting the energy to make it suitable for a variety of electrosurgical procedures.

2. Description of the Related Art

Electrosurgery involves application of high radio frequency (RF) electrical current to a surgical site to cut ablate, or coagulate tissue. In monopolar electrosurgery, a source or active electrode delivers radio frequency energy from the electrosurgical generator to the tissue and a return electrode carries the current back to the generator. In monopolar electrosurgery, the source electrode is typically part of a surgical instrument held by the surgeon and applied to the tissue to be treated. A patient return electrode is placed remotely from the active electrode to carry the current back to the generator.

In bipolar electrosurgery, a hand-held instrument typically carries two electrodes, e.g., electrosurgical forceps. One of the electrodes of the hand-held instrument functions as the active electrode and the other as the return electrode. The return electrode is placed in close proximity to the active (i.e., current supplying) electrode such that an electrical circuit is formed between the two electrodes. In this manner, the applied electrical current is limited to the body tissue positioned between the two electrodes.

In electrosurgery, radio frequency (RF) power is the preferred type of energy. However, RF energy must be generated having sufficient frequency, so that the RF energy may be used to cut, coagulate, etc. tissue by sustaining tissue thermal heating for prolonged periods of time. Current state of the art electrosurgical generators do not provide sufficiently powerful RF energy for prescribed periods of time. In addition, for each type of an electrosurgical procedure (e.g., monopolar, bipolar, vessel sealing) a different generator is used.

Therefore, there is a need for an electrosurgical generator which can develop high RF power with high efficiency and can be used to provide RF energy suitable for performing various types of electrosurgical procedures.

SUMMARY

The present disclosure provides for an electrosurgical generator that includes an RF output stage connected to a DC power supply. The RF output stage includes two connections that receive DC energy and are connected to a transformer. Each of the two connections includes a switching component that is cycled between on and off positions at the same frequency but in a 180 degrees out-of-phase relationship and a parallel inductor-capacitor resonant circuit. The two connections also include a series inductor-capacitor resonant circuit oriented at a primary winding of the transformer. The first connection generates a positive half-sinusoidal waveform and the second connection generates a 180 degrees phase-shifted positive half-sinusoidal waveform. The waveforms combine at the transformer to form a pure sine output waveform suitable for electrosurgical procedures involving RF energy.

According to one embodiment of the present disclosure, an electrosurgical generator is disclosed. The electrosurgical generator includes a power supply for generating a DC voltage. The electrosurgical generator also includes a first parallel inductor-capacitor circuit being driven by a first signal at a first predetermined frequency and a second parallel inductor-capacitor circuit driven by a second signal at the first predetermined frequency phase shifted 180 degrees. The electrosurgical generator further includes a series inductor-capacitor resonant circuit operably connected in series with a primary winding of a transformer. The first and second parallel inductor-capacitor circuits are operably connected to the transformer, such that the first inductor-capacitor circuit generates a positive half sine wave and the second inductor-capacitor circuit generates a 180 degrees phase-shifted positive half sine wave to generate a full sine wave in a secondary winding of the transformer.

According to another aspect of the present disclosure, a method for generating high frequency electrosurgical current is disclosed. The method includes the step of providing a power supply operable to generate a DC voltage, a first parallel inductor-capacitor circuit, a second parallel inductor-capacitor circuit, a series inductor-capacitor resonant circuit. The first parallel inductor-capacitor circuit, the second parallel inductor-capacitor circuit, and the series inductor-capacitor resonant circuit are operably connected in series with a primary winding of a transformer. The method also includes the steps of driving a first parallel inductor-capacitor circuit by a first signal at a first predetermined frequency; and driving a second parallel inductor-capacitor circuit by a second signal at the first predetermined frequency phase-shifted 180 degrees. The method further includes the steps of generating a positive half sine wave at the first inductor-capacitor parallel circuit, generating a 180 degrees phase-shifted positive half sine wave at the second parallel inductor-capacitor circuit, and combining the positive half sine wave and the 180 degrees phase-shifted positive half sine wave at the secondary winding of the transformer to generate a full sine wave.

According to a further aspect of the present disclosure a radio frequency (RF) output stage circuit is disclosed. The RF output stage circuit includes a first parallel inductor-capacitor circuit configured to generate a positive half sine wave driven by a first signal at a first predetermined frequency. The first parallel inductor-capacitor circuit being operably connected to a transformer which includes a first winding and a series inductor-capacitor resonant circuit connected in series to a second winding. The RF output stage circuit also includes a second parallel inductor-capacitor circuit configured to generate a 180 degrees phase-shifted positive half sine wave driven by a second signal at the first predetermined frequency phase-shifted 180 degrees. The second parallel inductor-capacitor circuit is operably connected to the transformer such that the positive half sine wave and the 180 degrees phase-shifted positive half sine wave are combined at the secondary winding of the transformer to generate a full sine wave.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure will be described herein below with reference to the accompanying drawings. In the following description, well-known functions or constructions are not described in detail to avoid obscuring the present disclosure in unnecessary detail.

The present disclosure includes an RF electrosurgical apparatus having a dual synchronous-resonant, magnetically coupled architecture which generates multi-mode and multi-frequency, monopolar, bipolar, and sealing type RF energy. RF energy is developed using a phase correlated dual drive network having a single or integer multiple number of drive pulses applies to switching devices which generate the dual synchronous-resonant RF energy, coupled in the magnetic field of a patient connective isolating transformer. Magnetically coupled RF energy is used to both generate the applied RF, used in clinical applications, and simultaneously cancel the unwanted parasitic RF harmonics during RF off periods. The RF harmonic unwanted energy is canceled when low duty cycle RF burst energy is repeatedly applied to the tissue site with a repetition rate frequency which is lower than the RF burst frequency. This architecture provides dynamic switching of high crest factor RF burst energy or low crest factor continuous sinusoidal RF delivered to the tissue for clinical efficacy to either individually coagulate blood vessels, seal vessels and cut tissue or simultaneously cut and coagulate tissue and vessels with hemostasis.

The generator according to the present disclosure can perform monopolar and bipolar electrosurgical procedures, including vessel sealing procedures. The generator includes a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

Figure 1A:
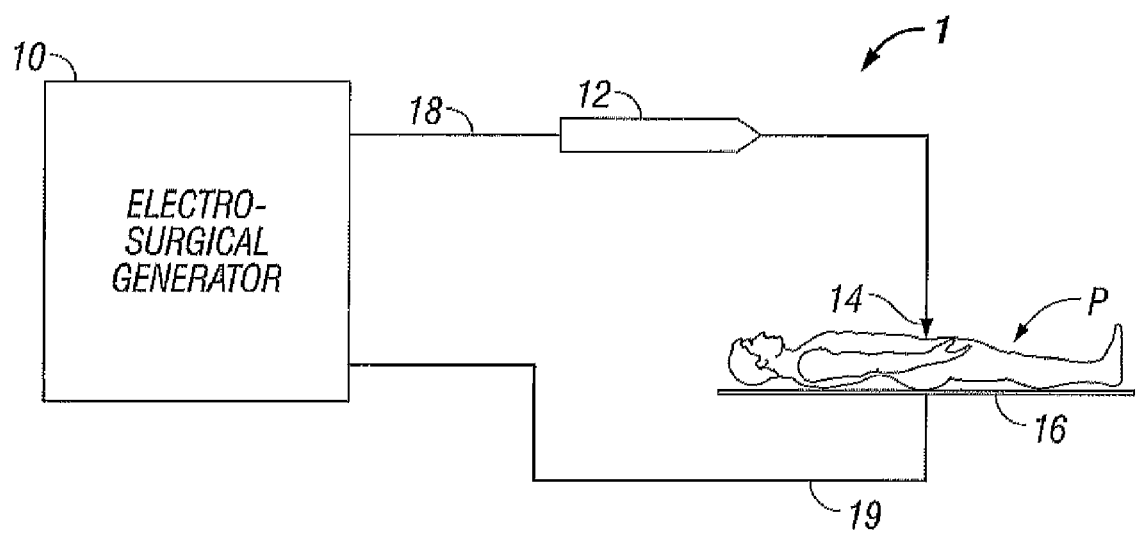
FIGS. 1A-1B are schematic block diagrams of an electrosurgical system according to the present disclosure.

FIG. 1A is a schematic illustration of an electrosurgical system 1 configured for a monopolar procedure. The system 1 includes an active electrode 14 and a return electrode 16 for treating tissue of a patient P. Electrosurgical RF energy is supplied to the active electrode 14 by a generator 10 via a cable 18 allowing the active electrode 14 to ablate, cut or coagulate the tissue. The return electrode 16 is placed at the patient P to return the energy from the patient P to the generator 10 via a cable 19.

The generator 10 includes input controls (e.g., buttons, activators, switches, etc.) for controlling the generator 10. The controls allow the surgeon to adjust power of the RF energy, waveform, and other parameters to achieve the desired waveform suitable for a particular task (e.g., cutting, coagulating, etc.). Disposed between the generator 10 and the active electrode 14 on the cable 18 is a hand piece 12, which includes a plurality of input controls which may be redundant with certain input controls of the generator 10. Placing the input controls at the hand piece 12 allows for easier and faster modification of RF energy parameters during the surgical procedure without having the surgeon divert his attention to the generator 10. It is also envisioned that a footswitch may be connected to the generator to control energy delivery during monopolar procedures.

Figure 1B:
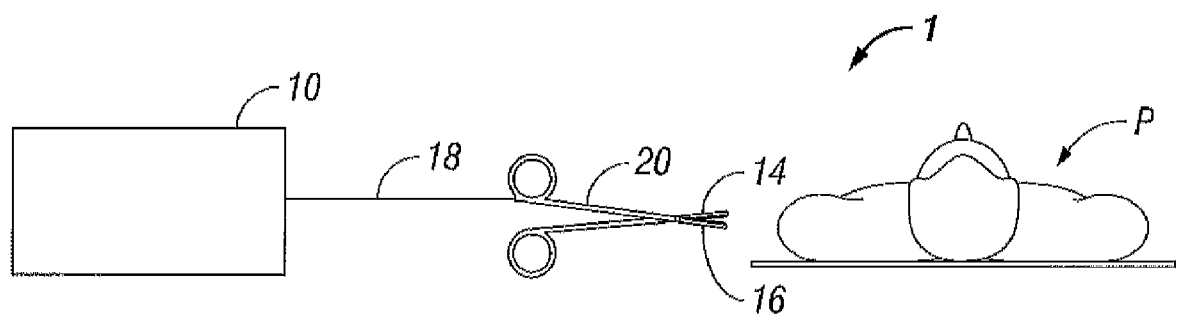

FIG. 1B is a schematic illustration of the electrosurgical system 1 configured for bipolar procedures. The active electrode 14 and the return electrode 16 are replaced by an electrosurgical forceps 20 which are connected to the generator 10 through the cable 18. More specifically, the electrosurgical forceps 20 include an active electrode 14 and a return electrode 16 disposed within jaws. The active electrode of the forceps 20 receives power from the cable 18 and the return electrode returns power via the cable 18.

Figure 2:
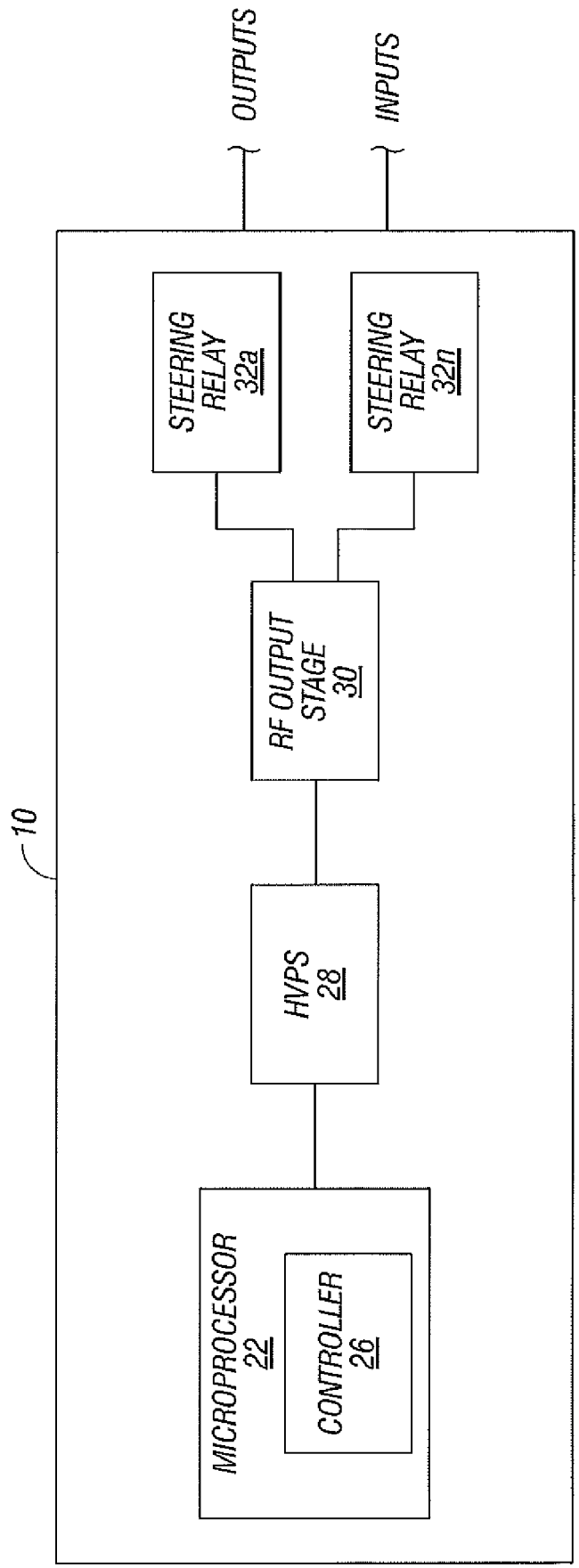
FIG. 2 is a schematic block diagram of a generator according to the present disclosure.

FIG. 2 shows a schematic block diagram of the generator 10 having a microprocessor 22, a high voltage DC power supply (HVPS) 28, and an RF output stage 30. The microprocessor 22 includes a controller 26 and an output port which is electrically connected to the HVPS 28 configured to supply DC voltage, from about 0 V to about 150 V, to the RF output stage 30. The microprocessor 22 receives input signals from the generator 10, the hand piece 12, or the footswitch and the controller 26, in turn, adjusts power outputted by the generator 10, more specifically the HVPS 28, and/or performs other control functions thereon.

The RF output stage 30 converts DC power into RF energy and delivers the RF energy, at about 470 KHz, to the active electrode 14, the forceps 20, or other electrosurgical devices connected to the generator 10. In addition, the RF output stage 30 also receives RF energy from the return electrode 16. More specifically, the RF output stage 30 is connected to one or more steering relays 32a-n. The steering relays 32a-n route RF energy from the RF output stage 30 to the multiple outputs of the generator 10, which may have a bipolar output configured for connection to the forceps 20, a monopolar output configured for connection to the active electrode 14, a footswitch output, etc. It is also envisioned that that the generator 10 may have multiple outputs of each type of output, e.g., the generator 10 can have two monopolar outputs and two bipolar outputs. This is particularly useful in electrosurgical procedures where multiple instruments are required (e.g., a smaller and a larger electrosurgical forceps configured for grasping tissue of various thicknesses). Only one output can be active at any one time, therefore, the steering relays 32a-n also provides isolation between the multiple outputs and their respective circuits.

Figure 3:
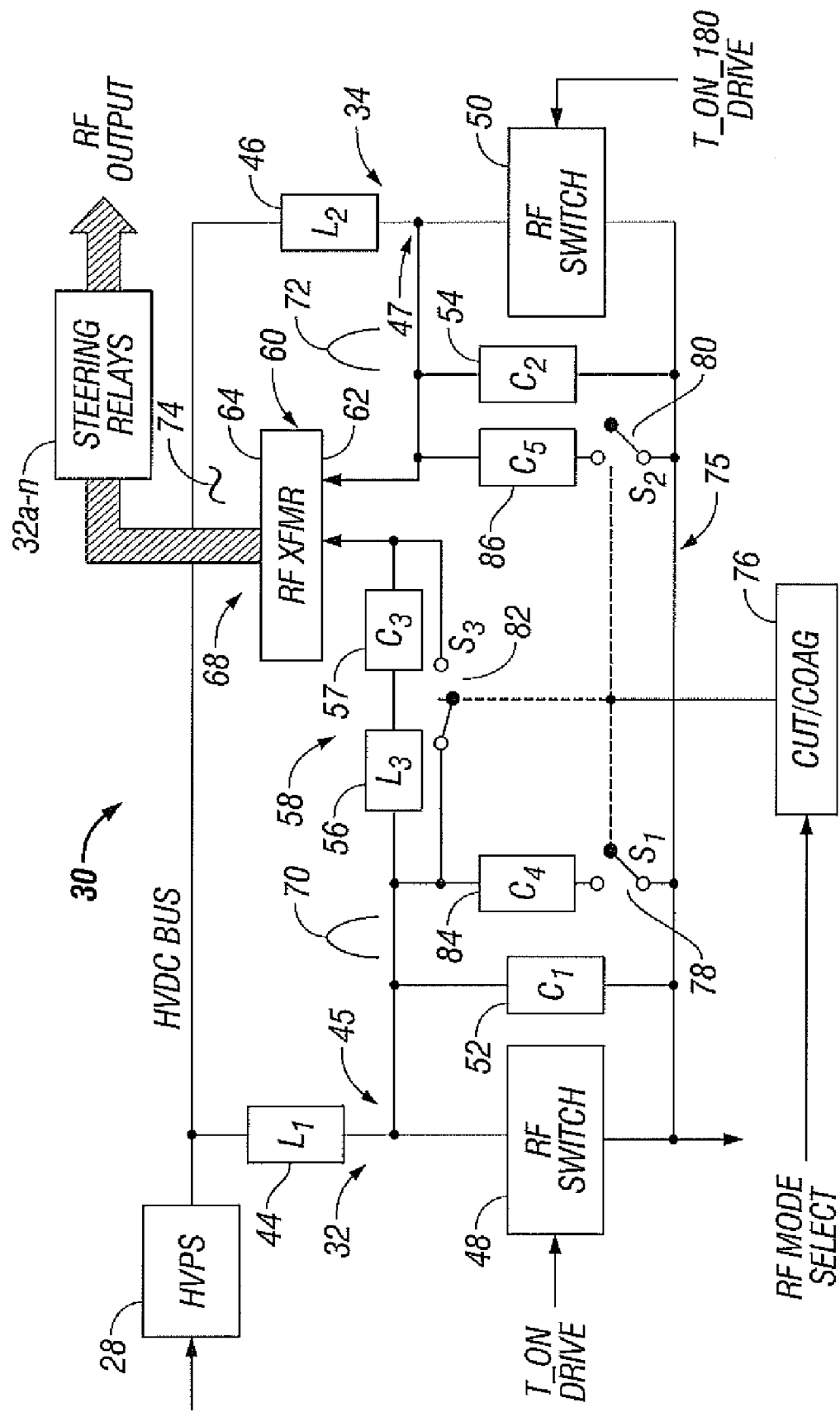
FIG. 3 is a circuit diagram of a radio frequency (RF) output stage according to the present disclosure.

The RF output stage 30 is shown in more detail in FIG. 3. The RF output stage 30 receives DC voltage from the HVPS 28 wherein first and second connections 32, 34 of a first winding 62 of a transformer 60 create two half-sinusoidal waveforms 180 degrees out-of-phase which then combine at a secondary winding 64 of the transformer 60 to form a pure (e.g., full) sinusoidal waveform.

The power of the HVPS 28 can be varied to modify RF magnitude (e.g., amplitude) thereby adjusting the power of the RF energy delivered to the tissue. This allows for accurate regulation of the power of delivered RF energy.

The first and second connections 32, 34 include switching components 48, 50 and parallel inductor-capacitor resonant circuits 45, 47 (parallel LC circuits 45, 47), respectively. The switching components 48, 50 can be, for example, transistors, such as metal-oxide semiconductor field-effect transistors (MOSFET), insulated gate bipolar transistors (IGBT), relays, and the like. The switching components 48, 50 are turned on and off at a predetermined frequency which is also the operating frequency of the generator 10, thereby closing and opening the first and second connections 32, 34 respectively. The frequency at which the switching components 48, 50 are turned on and off is controlled by a driver (not shown). The driver emits a phase-correlated (e.g., the switching components 48, 50 have a phase relationship) dual drive signal, (T_ON DRIVE and T_ON__180 DRIVE) more simply put, the driver signal cycles the switching components 48, 50 between on and off positions at the same frequency but out of sync, to create two half-sinusoidal waveforms 180 degrees out-of-phase. Therefore, adjusting the phase-correlated dual drive signal provides a means for varying operating RF frequency. Pulsing of the phase-correlated dual drive signal also provides means for RF duty cycle control.

Each of the first and second connections 32, 34 includes the parallel LC circuits 45, 47, respectively, which convert DC electrical energy into RF energy (e.g., AC energy having a high frequency from about 300 kHz to about 1000 kHz). The parallel LC circuits 45, 47 include inductors 44, 46 connected in parallel with first capacitors 52, 54 respectively. When the switching components 48, 50 are closed, DC power is supplied to the inductors 44, 46 which thereafter discharge through the first capacitors 52, 54, respectively, when the switching components 48, 50 are open. This process converts the constant pulse of DC energy into half-sinusoidal waveforms 70, 72 by the first and second connections 32, 34 respectively. Since the switching components 48, 50 turn on and off at the same frequency but 180 degrees out-of-phase, the resulting half-sinusoidal waveforms 70, 72 are also 180 degrees out-of-phase.

The first and second connections 32, 34 also include a series inductor-capacitor (LC) resonant circuit 58 which includes an inductor 56 and a capacitor 57 coupled to the second connection 34 of the primary winding 62. The series LC circuit 58 and the parallel LC circuits 45, 47 each have a resonant operating frequency which is mode dependant. The series resonant LC circuit 58 may be within 50 kHz of the operating frequency, which may be about 424 kHz. The parallel resonant LC circuits 45, 47 may be within 20 kHz of the operating frequency, which may be about 490 kHz. The resonant frequency is based on the inductance and capacitance values of the series LC circuit 58 and the parallel LC circuits 45, 47. The inductance of the inductors 44, 46, 56 and capacitance of the capacitors 52, 54, 57, 84, 86 should be selected to maximize the RF power developed for performing medical procedures. Inductors 44, 46 may be about 3.5 μhγ each, with inductor 56 at 44 μhγ. Capacitors 52, 54 may be both 0.025μf and capacitors 84, 86 may be both 0.033μf, with capacitor 57 having a value of 3.2 nf. The primary winding 62 inductance contributes to the series and parallel resonant LC tune and is optimized dependent on the delivered RF energy.

The inductor 56 and the capacitor 57 can be oriented in a plurality of ways. The alternate orientations have no effect on the functionality of the first and second connections 32, 34. In one embodiment, the inductor 56 and the capacitor 57 are coupled in series to the first connection 32, with the capacitor 57 coupled between the primary winding 62 and the inductor 56. It is also envisioned that the capacitor 57 is coupled to the second connection 34 and the inductor 56 is oriented to the first connection 32. In another embodiment, the capacitor 57 is coupled to the first connection 32 and the inductor 56 is coupled to the second connection 34. In a further embodiment, the inductor 56 and the capacitor 57 are coupled to the second connection 34, with the inductor 56 being oriented between the primary winding 62 and the capacitor 57.

As discussed above, the switching components 48, 50 are alternately switched on and off at the same frequency by the phase correlated dual drive signal (T_ON DRIVE and T_ON-.sub.—180 DRIVE). This synchronizes the parallel LC circuits 45, 47 and the series LC circuit 58 and develops the half-sinusoidal waveforms 70, 72. The half-sinusoidal waveform 70 is magnetically coupled through the transformer 60 to develop a positive half-sine voltage to a patient-connective side 68 leading to the active electrode 14. The half-sinusoidal waveform 72 is coupled through the transformer 60 to develop a second positive half-sine voltage. The half-sinusoidal waveforms 70, 72 combine on the secondary winding 64 (e.g., the patient-connective side 68) to generate a pure sine wave 74 because the half-sinusoidal waveforms 70, 72 are 180 degrees out-of-phase.

The RF output stage 30 also includes a switching circuit 75 for switching between multiple modes of operation of the generator 10, such as cutting, blending, division, fulguration, ablation, vessel sealing and coagulation. It is envisioned that certain modes can be used in bipolar and monopolar procedures (e.g., cutting, blending, division, etc.) while others are best suited for uses during specific procedures (e.g., ablation via monopolar and vessel sealing via bipolar).

The switching circuit 75 includes switches 78, 80, 82 and a capacitor 84 which along with the switch 78 is parallel with the capacitor 52 and a capacitor 86 which along with the switch 80 is parallel with the capacitor 54. The capacitors 84, 86 modify the waveform generated at the first and second connections 32, 34 when the switches 78, 80, 82 are closed. The switches 78, 80, 82 can be FET switches or relays. The capacitors 84, 85 modify the timing of the half-sine waveforms 70, 72 at connections 32, 34 by changing the resonant tune.

The switches 78, 80, 82 are controlled by a mode selection module 76 which receives control signals (e.g., selecting a specific mode) from the inputs of the generator 10 or the hand piece 12. Depending on which mode is chosen, the mode selection module 76 closes and/or opens corresponding switches. The cut mode is chosen with switches 78 and 80 closed and switch 82 open. Coagulation modes (e.g., blend, division with hemostasis, and fulgurate) operate with all of the switches 78, 80, 82 being in close position. Other modes are envisioned where the switch 82 is closed and switches 78 and 80 are open to achieve a higher tune parallel resonant network.

The RF output stage 30 is capable of generating a variety of waveforms suitable for performing specific electrosurgical procedures. For example, in cutting mode, the RF output stage generates a 473 kHz continuous sine wave with a crest factor of 1.5 or less, the duty cycle is 100%. In blend mode, the RF output stage 30 generates bursts of 473 kHz sine wave reoccurring at a 26.2 kHz rate, with the duty cycle of the bursts being 50%. In the blend mode, the crest factor of one period of the sine wave is less than 1.5 and the crest factor of the 26.2 kHz burst will be between 2.3 and 2.7. The division mode which is defined as "division with hemostasis," includes bursts of 473 kHz sine wave reoccurring at a 28.3 kHz rate, with the duty cycle being 25%; the crest factor of each of the 28.3 kHz bursts will be 3.2 to 4.3 with impedance being from about 100 Ohms to about 2,000 Ohms. The fulgurate mode includes bursts of 473 kHz sine wave reoccurring at a 30.7 kHz rate having a duty cycle of the bursts be about 6.5%; the crest factor of each of the bursts is from about 5.5 to about 7.2 with impedance being also from about 100 Ohms to about 2,000 Ohms.

The present disclosure provides for an electrosurgical generator which includes coupled series and parallel resonant LC networks. The LC networks permit development of high RF power without sacrificing high efficiency. In addition, the generator according to the present disclosure provides increasing lesion creation capability, more specifically, the generator allows for creation of larger ablation volumes in tissue. This is due to reduced power loss attributable to the coupled LC resonant topology, which minimizes the need for additional heat removal associated with high power RF energy generation processes. The dual resonant topology, with combined series and parallel LC resonant circuits provides efficient energy transfer between reactive LC component which consume minimal power loss. The LC network generates less heat as a result of the reactive impedance compared to the real power loss associated with resistive elements.

The electrosurgical generator according to the present disclosure provides many advantages. For example, the generator has multiple RF based operating modes (e.g., monopolar, bipolar, sealing, etc.) which produce suitable type RF energy from either single or multiple RF sources. The generator also generates synchronous-resonant RF energy, which is coupled in the magnetic field of the patient connective isolation transformer. Magnetically coupled RF energy is used to both generate the applied RF, used in clinical applications, and simultaneously cancel the unwanted parasitic RF harmonics during RF off periods, when low duty cycle RF burst energy is repeatedly applied to the tissue site with a repetition rate frequency lower than the RF burst frequency. Magnetic coupling of the dual resonant RF also creates automatic damping of RF ring energy during off periods, without the need for damping components with low duty cycle coagulation waveforms applied to tissue loads.

In particular, the RF topology illustrated in FIG. 3 is uniquely configured such that the synchronously phased waveforms of 70, 72 generate in-sync ripple components, impressed upon the primary 62 winding of the transformer 60 at the completion of their respective half-sine waveforms. These ripple voltages generate an opposing magnetic field coupling in the primary winding 62 equivalent to the common mode rejection principle, such that the unwanted parasitic RF harmonics do not transfer to the secondary winding 64 of the patient connective transformer 60. As a result, the RF output stage 30 automatically cancels the parasitic RF content during the RF off periods, independent of the variable low duty RF waveforms, for the RF modes such as blend, fulgurate, division with hemostasis, spray, etc.

The generator also allows for dynamic RF switching of high crest factor RF burst energy or low crest factor continuous sinusoidal RF delivered to the tissue. This allows for clinical efficacy to either individually coagulate or seal vessels and cut tissue or simultaneously cut and coagulate tissue and vessels with hemostasis. The generator also provides additional advantages: 1) the generator provides multiple RF operating frequencies from a single RF source by altering tuning of the RF; 2) the generator provides a phase correlated dual drive network, having singular and integer multiple number of drive pulses applied to switching device which generate the dual synchronous-resonant RF energy; 3) the generator provides RF operating modes are selected and processed on the ground referenced primary side of the patient connective isolation transformer thereby providing a fast RF response for clinical applications; 4) the generator does not allow energy storage or filter components to be present on the patient connective output; 5) there are no RF output surging or back emf effects result with rapid tissue desiccation and arcing due to the removal of output energy storage and filter components; 6) the generator provides controlled RF delivery in the presence of delivered arc energy; and 7) the generator provides high immunity to disruptive arc energy in vessel sealing mode due to the elimination of output energy storage and filter components.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. An electrosurgical generator comprising:
   a power supply operable to generate a DC voltage;
   a first parallel inductor-capacitor circuit configured to be driven by a first signal at a first predetermined frequency;
   a second parallel inductor-capacitor circuit configured to be driven by a second signal at the first predetermined frequency phase-shifted 180 degrees; and
   a series inductor-capacitor resonant circuit operably connected in series with a primary winding of a transformer, the first and second parallel inductor-capacitor circuits operably connected to the transformer, the first parallel inductor-capacitor circuit being configured to generate a positive half sine wave from the DC voltage and the second parallel inductor-capacitor circuit being configured to generate a 180 degrees phase-shifted positive half sine wave from the DC voltage to generate a full sine wave in a secondary winding of the transformer.

2. An electrosurgical generator as in claim 1, wherein the first parallel inductor-capacitor resonant circuit is tuned to a first self-resonant frequency that is substantially equivalent to the first predetermined frequency.

3. An electrosurgical generator as in claim 2, wherein the first parallel inductor-capacitor resonant circuit includes a first inductor having a first inductance value and a first capacitor having a first capacitance value, wherein the first inductance value and the first capacitance correspond to the first self-resonant frequency.

4. An electrosurgical generator as in claim 1, wherein the second parallel inductor-capacitor resonant circuit is tuned to a second self-resonant frequency that is substantially equivalent to the first predetermined frequency.

5. An electrosurgical generator as in claim 4, wherein the second parallel inductor-capacitor resonant circuit includes a second inductor having a second inductance value and a second capacitor having a second capacitance value, wherein the second inductance value and the second capacitance correspond to the second self-resonant frequency.

6. An electrosurgical generator as in claim 1, wherein the first and second parallel inductor-capacitor circuit are driven by switching on and off first and second switching components respectively.

7. An electrosurgical generator as in claim 6, wherein the first and second switching components are selected from the group consisting of transistors, relays, metal-oxide semiconductor field-effect transistors and insulated gate bipolar transistors.

8. An electrosurgical generator as in claim 1, wherein the series inductor-capacitor resonant circuit is tuned to a third self-resonant frequency that is substantially equivalent to the first predetermined frequency.

9. An electrosurgical generator as in claim 8, wherein the series inductor-capacitor resonant circuit includes a third inductor having a third inductance value and a third capacitor having a third capacitance value, wherein the third inductance value and the third capacitance correspond to the third self-resonant frequency.

10. A method for generating high frequency electrosurgical current comprising the steps of:
- providing a power supply operable to generate a DC voltage, a first parallel inductor-capacitor circuit, a second parallel inductor-capacitor circuit, a series inductor-capacitor resonant circuit, wherein the first parallel inductor-capacitor circuit, the second parallel inductor-capacitor circuit, and the series inductor-capacitor resonant circuit are operably connected in series with a primary winding of a transformer;
- driving the first parallel inductor-capacitor circuit by a first signal at a first predetermined frequency;
- driving the second parallel inductor-capacitor circuit by a second signal at the first predetermined frequency phase-shifted 180 degrees; and
- generating a positive half sine wave at the first inductor-capacitor parallel circuit;
- generating a 180 degrees phase-shifted positive half sine wave at the second parallel inductor-capacitor circuit; and
- combining the positive half sine wave and the 180 degrees phase-shifted positive half sine wave at a secondary winding of the transformer to generate a full sine wave.

11. A method as in claim 10, wherein the first parallel inductor-capacitor resonant circuit of the providing step is tuned to a first self-resonant frequency that is substantially equivalent to the first predetermined frequency.

12. A method as in claim 11, wherein the first parallel inductor-capacitor resonant circuit of the providing step includes a first inductor having a first inductance value and a first capacitor having a first capacitance value, wherein the first inductance value and the first capacitance correspond to the first self-resonant frequency.

13. A method as in claim 10, wherein the second parallel inductor-capacitor resonant circuit of the providing step is tuned to a second self-resonant frequency that is substantially equivalent to the first predetermined frequency.

14. A method as in claim 13, wherein the second parallel inductor-capacitor resonant circuit includes a second inductor having a second inductance value and a second capacitor having a second capacitance value, wherein the second inductance value and the second capacitance correspond to the second self-resonant frequency.

15. A method as in claim 10, wherein the first and second parallel inductor-capacitor circuits of the providing step are each driven in the respective driving steps by switching on and off first and second switching components respectively.

16. A method as in claim 15, wherein the first and second switching components are selected from the group consisting of transistors, relays, metal-oxide semiconductor field-effect transistors and insulated gate bipolar transistors.

17. A method as in claim 10, wherein the series inductor-capacitor resonant circuit of the providing step is tuned to a third self-resonant frequency that is substantially equivalent to the predetermined frequency.

18. A method as in claim 17, wherein the series inductor-capacitor resonant circuit of the providing step includes a third inductor having a third inductance value and a third capacitor having a third capacitance value, wherein the third inductance value and the third capacitance correspond to the third self-resonant frequency.

19. A radio frequency output stage circuit, comprising:
- a first parallel inductor-capacitor circuit configured to generate a positive half sine wave driven by a first signal at a first predetermined frequency, the first parallel inductor-capacitor circuit being operably connected to a transformer which includes a first winding and a series inductor-capacitor resonant circuit connected in series to a second winding;
- a second parallel inductor-capacitor circuit configured to generate a 180 degrees phase-shifted positive half sine wave driven by a second signal at the first predetermined frequency phase-shifted 180 degrees, the second parallel inductor-capacitor circuit being operably connected to the transformer such that the positive half sine wave and the 180 degrees phase-shifted positive half sine wave are combined at the secondary winding of the transformer to generate a full sine wave.

* * * * *